United States Patent [19]

Gilman

[11] 4,289,144
[45] Sep. 15, 1981

[54] A-V SIDEARM LEAD

[75] Inventor: Byron L. Gilman, Maple Grove, Minn.

[73] Assignee: Medtronic, Inc., Minneapolis, Minn.

[21] Appl. No.: 111,049

[22] Filed: Jan. 10, 1980

[51] Int. Cl.$^3$ .............................................. A61N 1/04
[52] U.S. Cl. ................................ 128/785; 128/419 P; 128/786
[58] Field of Search ..................... 128/419 P, 784–786

[56] References Cited

U.S. PATENT DOCUMENTS

| 3,649,367 | 3/1972 | Purdy | 128/419 P |
| 3,865,118 | 2/1975 | Burgs | 128/419 P |
| 3,902,501 | 9/1975 | Chron et al. | 128/785 |
| 3,939,843 | 2/1976 | Smyth | 128/419 P |
| 4,057,067 | 11/1977 | Lajos | 128/419 P |
| 4,072,154 | 2/1978 | Anderson et al. | 128/419 P |

FOREIGN PATENT DOCUMENTS

| 9732 | 9/1979 | European Pat. Off. | 128/785 |
| 2605590 | 8/1977 | Fed. Rep. of Germany | 128/419 P |

Primary Examiner—William E. Kamm
Attorney, Agent, or Firm—John L. Rooney; Lew Schwartz; Joseph F. Breimayer

[57] ABSTRACT

Atrial-ventricular coaxial transvenous pacing lead including an inner ventricular lead having an electrode and an outer atrial lead having an atrial sidearm lead, the atrial sidearm lead including a sigmoidal shape and an electrode at the distal end of the sidearm lead. Outwardly extending tines can surround either or both of the electrodes. The atrial sidearm lead maintains geometrical memory of the sigmoidal shape. The atrial sidearm head can be used absent the ventricular lead.

15 Claims, 4 Drawing Figures

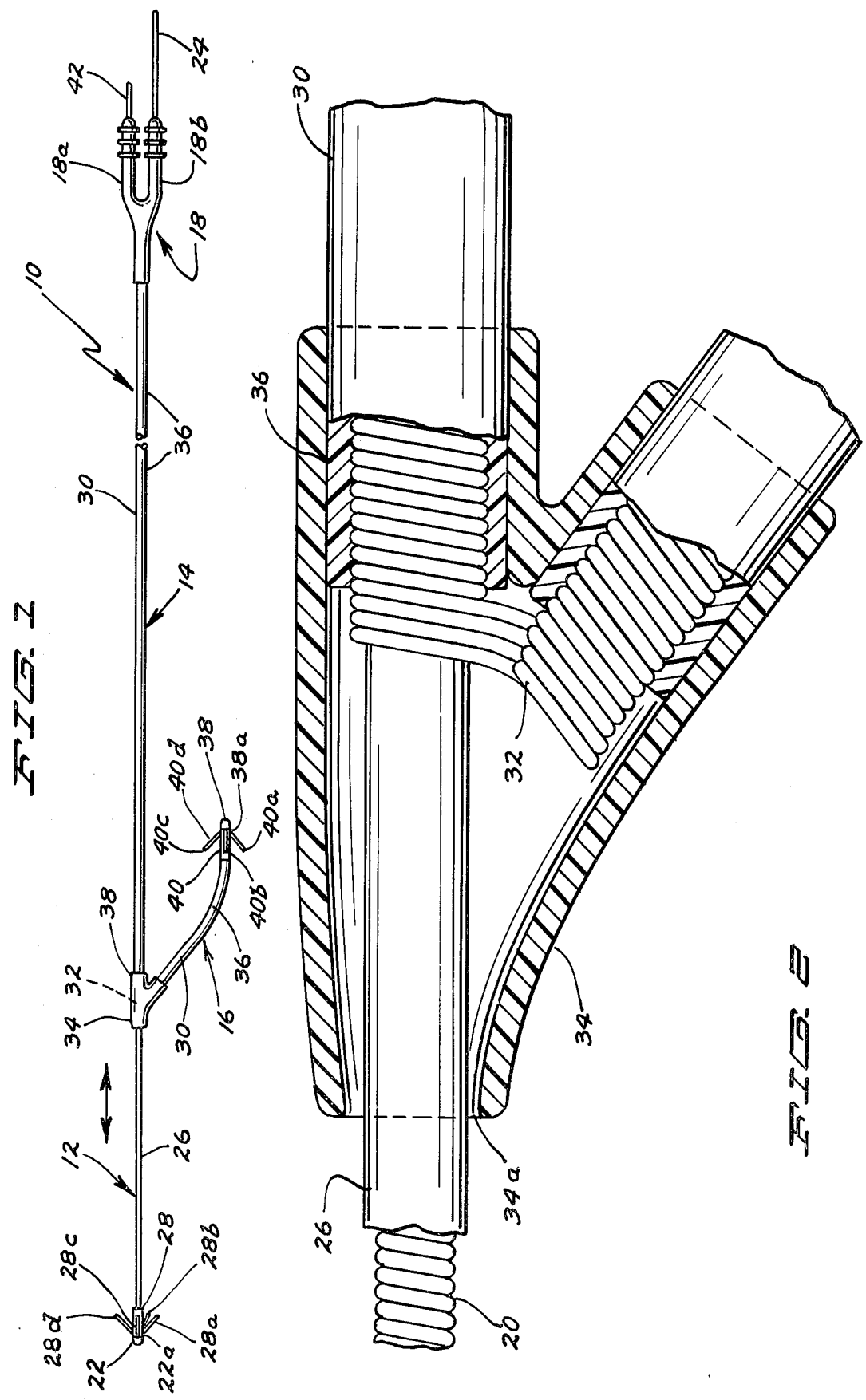

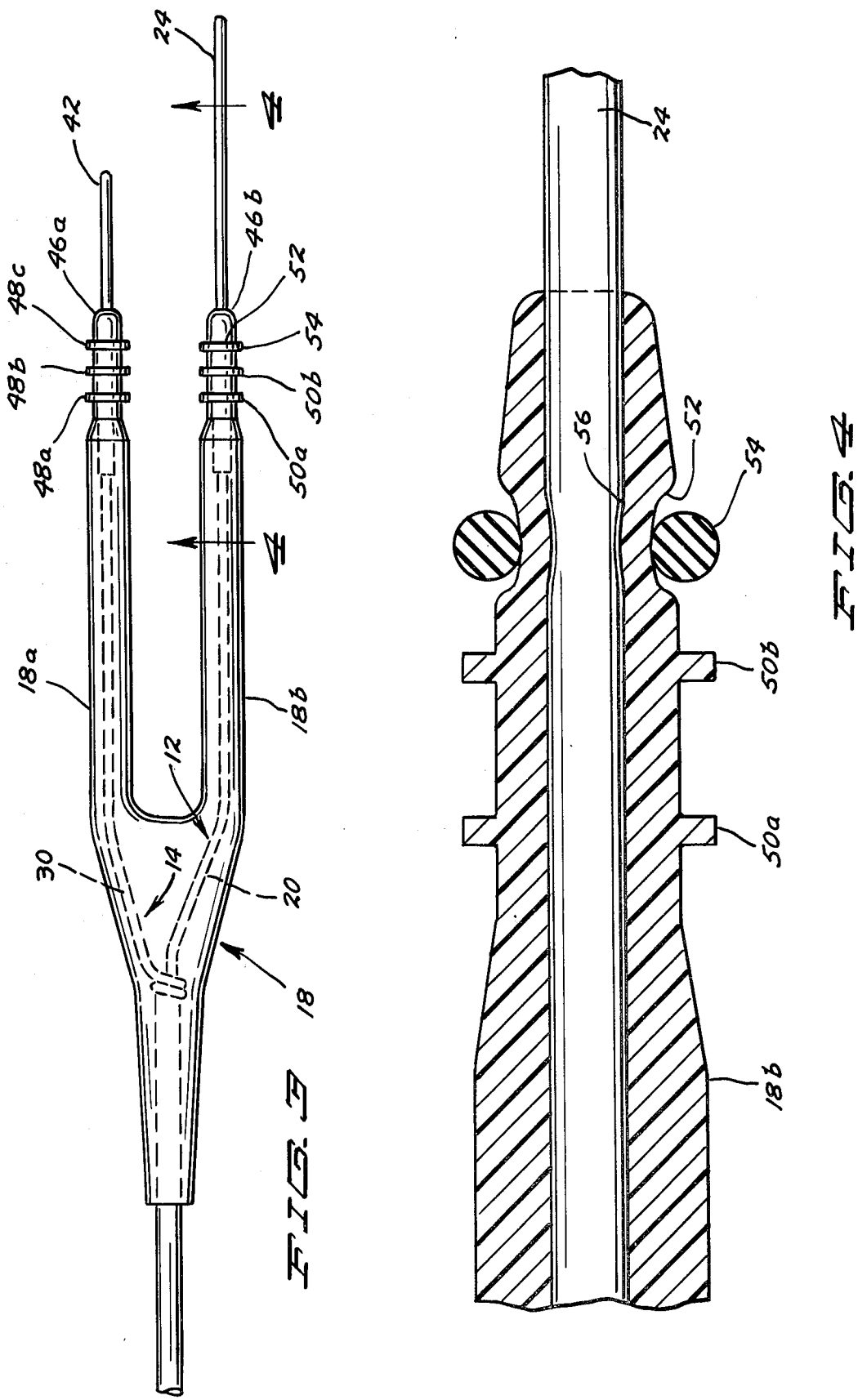

A-V SIDEARM LEAD

CROSS REFERENCES TO CO-PENDING APPLICATIONS

None.

DESCRIPTION OF THE PRIOR ART

1. Field of the Invention

The invention relates to a surgical electrode, and more particularly, pertains to an atrial ventricular sidearm coaxial pacing lead.

2. Background of the Invention

It has been a common practice in the prior art to use two different leads passed through a vein or veins to perform atrial-ventricular pacing. The passage of the two separate leads has not only been a problem from a surgical standpoint, but also a problem from a pacing standpoint of not only passage of the leads through the vein but connection to a pulse generator.

Other prior art leads would be passed through the vein or veins, and pace the superior vena cava in addition to the ventricular chamber. Positioning in the superior vena cava is metastable.

The present invention relates to an atrial ventricular coaxial sidearm pacing lead where the atrial sidearm pacing lead coaxially slides over the ventricular lead thereby forming a coaxial lead.

SUMMARY OF THE INVENTION

The present invention provides an atrial ventricular sidearm coaxial lead for A-V pacing.

According to one embodiment of the present invention, there is provided an atrial ventricular coaxial sidearm lead including an inner coaxial ventricular lead, and an outer conductor atrial sidearm lead having memory of geometrical shape.

One significant aspect and feature of the present invention is an A-V coaxial sidearm lead where the atrial electrode is on an outer conductor of a coaxial pacing lead positioned at one end of the sidearm.

Another significant aspect and feature of the present invention is an atrial ventricular coaxial sidearm lead wherein the electrode is located at the end of the sidearm, the sidearm being geometrically shaped to position itself within the atrial chamber. The sidearm is a relatively stiff coil which can retain a predetermined geometrical shape. The atrial sidearm springs away from the atrial lead when unrestricted allowing for precise placement in the atrial appendage and without the use of a stylet providing for increased stability.

A further significant aspect and feature of the present invention is an atrial ventricular coaxial pacing lead where the atrial sidearm includes an outer coaxial coil having a stiffness property for memory of the geometrical size and shape. An S sigmoidal curve by way of example and for purposes of illustration only remains lodged over a wider range of lead body motions providing that the pacing tip remains in the same position. The geometrical shape can also be characterized as an S shape, recurved, barbed, etc. This geometrical shape transmits less force. Trauma to the heart is reduced and chronic thresholds are lower than other types of leads. The S shape provides for a more stable electrode position as the transmission of tension and torque is reduced.

A further significant aspect and feature of the present invention is an atrial sidearm for an atrial ventricular coaxial sidearm lead for the geometric shape of the atrial sidearm is an S-curve which prevents perforation of the atrial chamber wall. The ring tip electrode of the atrial sidearm can have tines by way of example and for purposes of illustration only or in the alternative can just be an electrode affixed to the end of the sidearm coil.

An additional significant aspect and feature of the present invention is an atrial sidearm having a reverse foldback connection at the end of the outer coaxial coil and the other end of the atrial sidearm. This further enhances the memory of geometrical size and shape and provides for passage through a vein, passage through the heart, and subsequent placement of the atrial sidearm lead in the atrial chamber of the heart. There is continuous electrical communication and electrical connection by reversing and folding back the atrial sidearm so that the wire strands are continuous and uninterrupted providing for long flexible life of the atrial sidearm lead.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the FIGURES thereof and wherein:

FIG. 1 illustrates a plan view of transvenous leads with an atrial sidearm;

FIG. 2 illustrates an exploded view of a reverse foldback winding of a lead;

FIG. 3 illustrates an electrical connector; and

FIG. 4 illustrates a cross-sectional view taken along line 4—4 of FIG. 3.

DETAILED DESCRIPTION OF THE PREFERRED EMBODIMENTS

FIG. 1, which illustrates a plan view of a ventricular lead with an atrial lead including an atrial sidearm of the present invention, shows an atrial-ventricular lead 10 including a ventricular lead 12, an atrial lead 14, an atrial sidearm 16, and a connector 18. The ventricular lead 12 includes a quadra-filar space wound coil 20 such as an MP35N alloy by way of example and for purposes of illustration only extending a longitudinal distance, a ventricular electrode 22 such as a ring tip electrode by way of example and for purposes of illustration only secured to one end of the wound coil 20 and a proximal tip 24 at the other end of the wound coil 20. A polyurethane insulation coating 26 as illustrated in FIG. 2 extends the distance of the wound coil 20 between the electrode 22 and the proximal tip 24. A tine support body 28 including a plurality of outwardly extending tines 28a–28d by way of example and for purposes of illustration only axially secures over the electrode 22 and abuts against a shoulder 22a. The other end of the ventricular lead 12 slides through one connector sleeve 18b of the connector 18 as later described in detail in FIGS. 3 and 4. A quadra-filar space wound coil 30 of similar structure and of a larger diameter than of the wound coil 20 coaxially extends over the polyurethane insulation coating 26 of ventricular lead 12 and is shorter in longitudinal length with respect to the ventricular lead 12. An atrial sidearm lead 16 connects in a reverse foldback winding 32 as also illustrated in FIG. 2 and forms a geometrical shape having memory of the sigmoidal geometrical shape as illustrated in the figure. The geometric shape of the atrial sidearm lead 16 is sigmoidal in shape by way of example and for purposes of illustration only, and can assume any other geometrical shape as so predetermined. The atrial sidearm 16 is constructed and formed so that the arm 16 maintains the memory of the physical shape. The atrial sidearm lead 16 is a continuation of the quadra-filar space wound coil 30 including the polyurethane insulation coating 36. An insulation boot 34 extends over the reverse foldback winding 32 and takes a narrow geometrical shape. An atrial electrode 38 is located at and connects to a pacing tip end of the wound coil 30 of the atrial sidearm lead 16. The electrode 38 can be either a ring tip electrode or a canted electrode by way of example and for purposes of illustration only. A tine support body 40 including tines 40a–40d illustrated in FIG. 2 is axially secured to the atrial electrode 38 and abuts against a shoulder 38a of the atrial electrode 38. A connector pin 42 connects to the proximal end of the wound coil 30, and the connector pin 42 is secured in the other connector sleeve 18a.

FIG. 2 illustrates an exploded view of the reverse foldback winding 32 there all elements correspond to those elements previously delineated. The space 34a between the front of the insulation boot and the ventricular lead 12 is such as to loosely engage and also provide a few thousandths of an inch of clearance for coaxial sliding between the leads 12 and 14.

FIG. 3, which illustrates the electrical connector 18, shows the wound coil 30 of the atrial lead 14 electrically affixed to a connector pin 42 through the sleeve 18a of the elongated "Y" connector 18. The end 46a of the sleeve 18a is configured to functionally engage in a connector block of a pulse generator not illustrated in the figure. Sealing rings 48a, 48b and 48c by way of example and for purposes of illustration only provide a seal between the pulse generator and the sleeve 18a. Adhesive can be injected between the sleeve 18a and the connector pin 42 further sealing the two members together. The wound coil 20 including the polyurethane insulation coating 26 of the ventricular lead 12 slides through the sleeve 18b of the connector 18 for a finite distance beyond the end 46b of the sleeve 18b. Two sealing rings 50a and 50b are likewise provided on the other end 46b. An O-ring groove 52 positions between the sealing ring 50b and the end 46b as also illustrated in FIG. 4 and accepts an O-ring 54 which forms a liquid seal 56 between the sleeve 18b and the polyurethane insulation coating 26 of the wound coil 20.

FIG. 4, which illustrates the cross sectional view taken along line 4—4 of FIG. 3, shows numerals corresponding to elements previously delineated.

PREFERRED MODE OF OPERATION

The atrial-ventricular lead 10 with the atrial sidearm lead 16 is inserted in through an appropriate vein in the human body towards the heart with the aid of a stylet and fluoroscope for precise positioning of the lead. Initially, the atrial-ventricular lead 10 is pushed in a joint relationship, with the ventricular pacing tip 22 extending ahead of the insulation boot 34, until the ventricular lead 12 lodges in the apex of the right ventricle. Then, the atrial lead 14 with the attached atrial sidearm 16 is pulled so as to lodge in the atrium of the heart by appropriately pulling the atrial sidearm 16 up and into the atrial appendage after being pushed down beyond the precava-atrial junction of the heart thereby providing a sensory digital feedback signal to the medical personnel. Once proper positioning of the lead 10 has been achieved with the ventricular lead sliding within the other sleeve 18b of the connector 18, the O-ring 54, is positioned on the O-ring groove 52 thereby frictionally engaging the other sleeve 18b of the connector 18 to the polyurethane insulation coating 26 of the wound coil 20 of the ventricular lead 12. Subsequently the proximal tip 24 and the connector pin 40 is electrically connected to the pulse generator for subsequent pacing of the individual's heart.

The French size of the ventricular lead 12 can be in the range of 7–10 French by way of example and for purposes of illustration only while the atrial sidearm lead 14–16 can be in the range of 9–16 French by way of example and for purposes of illustration only without departing from the apparent scope of the present invention. The atrial lead 14 with the atrial sidearm 16 can be utilized independently of the ventricular lead 12 for atrial sensing and/or pacing. Suitable additional electrodes such as ring electrodes can be added to either the ventricular lead 12, the atrial lead 14, or the atrial sidearm lead 16 as so predetermined.

Having thus described the invention, there is claimed as new and desired to be secured by Letters Patent:

1. Atrial-ventricular sidearm transvenous pacing lead for supplying stimulating signals to an atrium cavity and a ventricular cavity comprising:
   a. ventricular lead including first a space-wound coil, insulation covering said first space-wound coil, a ventricular electrode secured to a distal end of said first space-wound coil and a proximal tip secured to a proximal end;
   b. atrial lead including a second space-wound coil slideably mounted in coaxial relation over said first space-wound coil and insulation covering said second space-wound coil and a proximal tip secured to the proximal end; and
   c. atrial sidearm lead including a space-wound coil having a geometrical memory shape, means connecting said distal end of said sidearm lead to said distal end of said atrial lead, insulation covering said space-wound coil of said lead, and an atrial electrode affixed to a pacing tip of said atrial sidearm lead whereby said ventricle lead coaxially slides within said atrial lead for positioning of said ventricular electrode into said ventricular cavity and said atrial electrode into said atrial cavity.

2. The lead of claim 1 comprising a plurality of tines surrounding said ventricular electrode.

3. The lead of claim 1 wherein said ventricular electrode is a ring-tip electrode.

4. The lead of claim 1 comprising a plurality of tines surrounding said atrial electrode.

5. The lead of claim 1 wherein said atrial electrode is a ring-tip electrode.

6. The lead of claim 1 wherein said atrial electrode is a canted electrode.

7. The lead of claim 1 wherein said connecting means is a continuous reverse foldback connection.

8. The lead of claim 7 comprising an insulating connector boot covering said reverse foldback connection.

9. The lead of claim 1 wherein said atrial sidearm lead is of sigmoidal shape.

10. The lead of claim 1 wherein said ventricular lead is of a diameter in the range of 7–10 French.

11. The lead of claim 1 wherein said atrial lead and atrial sidearm lead is of a diameter in the range of 9-16 French.

12. Atrial-ventricular sidearm transvenous pacing lead comprising:
   a. ventricular lead including a first space-wound coil, insulation covering said first space-wound coil, ring-tip electrode secured to one end of said first space-wound coil, and a plurality of tines extending outwardly from said ring-tip electrode;
   b. atrial lead including a second space-wound coil slideably mounted in coaxial relation over said first space-wound coil and insulation covering said second space-wound coil; and
   c. atrial sidearm lead including a space-wound coil having a geometrical memory shape, a reverse foldback connecting said distal end of said sidearm lead to said distal end of said atrial lead, insulation covering said space-wound coil, a ring-tip electrode affixed to a pacing tip of said atrial sidearm lead, and a plurality of tines extending outwardly from said ring-tip electrode.

13. The lead of claim 12 comprising:
   a. connector pin secured to the end of said atrial lead;
   b. proximal tip secured to the end of said ventricle lead; and
   c. connector including two elongated sleeves encompassing and secured to said connector pin, the other of said connector sleeve surrounding and permitting sliding movement of said ventricular lead therethrough and means to secure said sleeve to said ventricular lead.

14. The lead of claim 13 wherein said securing means comprises an O-ring groove in said other sleeve and an O-ring which fits into said O-ring groove whereby said O-ring forms a liquid seal between said connector sleeve and said ventricular lead.

15. A body implantable lead comprising:
   a first conductor having a proximal end and having a distal end with an electrode attached thereto;
   a second conductor having a proximal end and having a distal end with an electrode attached thereto and having a point intermediate said proximal end and said distal end such that said second conductor is slideably mounted coaxially about said first conductor from said proximal end of said second conductor to said point and said second conductor is angularly displaced from said first conductor from said point to said distal end of said second conductor at an obtuse angle relative to said distal end of said first conductor and said first conductor and said second conductor are mutually insulated.

* * * * *